United States Patent [19]

Hall

[11] 4,321,781
[45] Mar. 30, 1982

[54] PROCESS FOR PRODUCING A PACKAGE
[75] Inventor: Rolande E. Hall, Shannon, Ireland
[73] Assignee: Howmedica Management & Technical Services, Limited, Stanmore, England
[21] Appl. No.: 155,229
[22] Filed: Jun. 2, 1980

Related U.S. Application Data

[63] Continuation of Ser. No. 948,475, Oct. 4, 1978, abandoned.

[30] Foreign Application Priority Data

Oct. 12, 1977 [GB] United Kingdom ............... 42352/77

[51] Int. Cl.³ .......................................... B65B 11/52
[52] U.S. Cl. ..................................... 53/427; 206/471
[58] Field of Search ................ 53/425, 141, 427, 509; 206/471

[56] References Cited

U.S. PATENT DOCUMENTS

| | | | |
|---|---|---|---|
| Re. 26,494 | 12/1968 | Stoker | 206/419 |
| 3,031,072 | 4/1962 | Kraut | 53/427 X |
| 3,358,829 | 12/1967 | Smith et al. | 53/427 X |
| 3,481,101 | 12/1969 | Steadman | 53/471 |
| 3,547,257 | 12/1970 | Armentrout | 206/439 |
| 3,726,057 | 4/1973 | Kemble | 53/449 X |
| 3,926,311 | 12/1975 | Laske | 206/439 |
| 4,055,454 | 10/1977 | Laske | 156/290 |

FOREIGN PATENT DOCUMENTS

| | | | |
|---|---|---|---|
| 1152475 | 2/1968 | France | 53/427 |
| 49-42683 | 10/1974 | Japan | 53/427 |
| 1412375 | 11/1975 | United Kingdom | 53/427 |

*Primary Examiner*—R. L. Spruill
*Assistant Examiner*—Charles L. Willis
*Attorney, Agent, or Firm*—Diller, Ramik & Wight

[57] ABSTRACT

A process of producing a package for a product by heat-bonding through a heat sealable coating a first wall of porous spun bonded polyolefin material to a second and thicker wall of porous material, placing a product atop the first wall, draping a thermoformable film over the product, heating the film, drawing the film against the product and the first wall, and bonding the drawn film to the first wall during the drawing operation.

7 Claims, 4 Drawing Figures

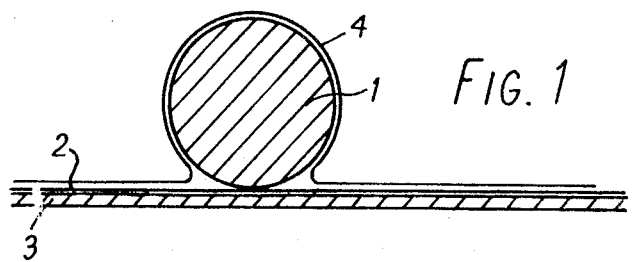
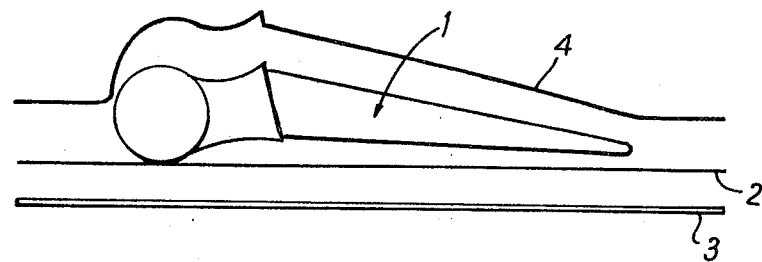
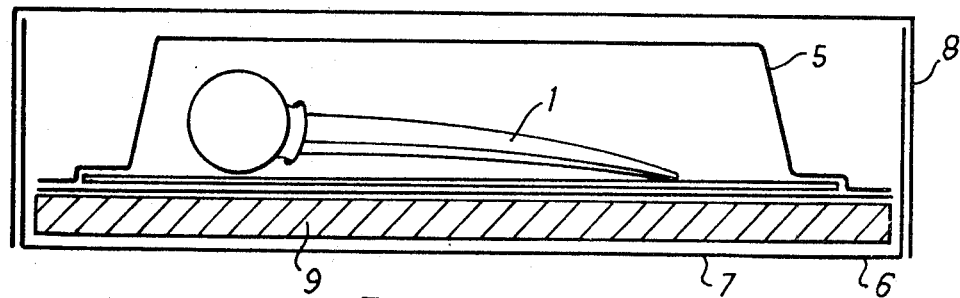
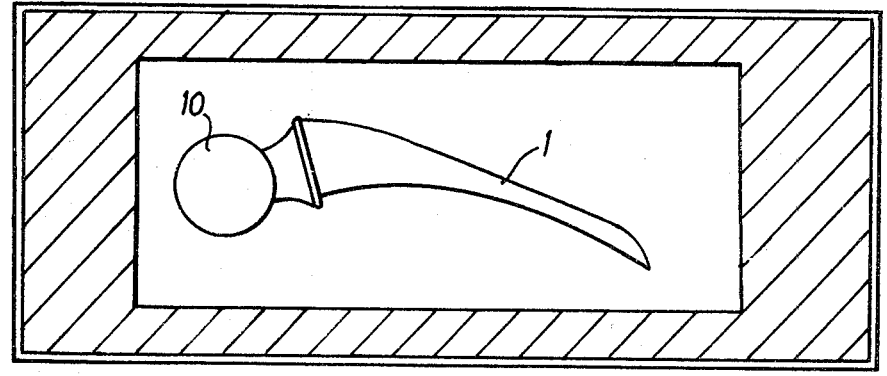

PROCESS FOR PRODUCING A PACKAGE

This is a continuation of application Ser. No. 948,475, filed Oct. 4, 1978, and now abandoned.

This invention relates to a process for producing a package for a product and to a package produced by such a process.

The invention is particularly although not exclusively applicable to the packaging of a surgical implant so that the implant can be held under sterile conditions and the packaging is such that the sterilisation of the product can take place after manufacture, for example by gamma irradiation, the packaging enabling sterile conditions to be maintained during distribution and subsequent storage until the package is opened. A further advantage of the package according to the invention is that it allows product visibility, is well suited for the protection of sterile disposables and it can provide an easy open peelable seal.

Packages containing such a surgical implant and which are at present used for distribution usually contain two barrier layers to resist penetration of bacteria, the outer layer being removed under clean conditions by a circulating nurse who does not touch the inner barrier layer, the inner barrier layer is only handled and opened to expose its contents in sterile conditions using aseptic handling techniques. The present methods of producing these packages generally result in packages which do not render the implant fully visible or which require the use of an instrument to cut through the barrier layers and such instruments can be the cause of sterility breakdown by transfer of bacteria from the exterior to the interior of the barrier across the opening cut. A further method which is sometimes used is to pack such products in preformed plastics material bubbles or blisters but as a different shape is required for each product. This can prove to be too expensive for short production runs.

In conventional skin packaging the product is placed on a sheet of paperboard or carboard which is sometimes heat seal coated and a thermo-formable film softened by radiant heat is draped over the product and drawn by a vacuum to follow the contours of the product heat sealing itself to the board where they are in mutual contact. In this method the vacuum is drawn through the paperboard and the board must therefore be porous. The disadvantage of this method when applied to a package which has to be sterile is that the cardboard is not bacteria resistant and that it is difficult to open. The applicant has found however that the cardboard in such a package can be replaced by a material which is bacteria resistant but which at the same time is porous enough to allow the vacuum to be drawn through it. The process also produces a "peel seal" which allows the thermo-formable film to be peeled from the spun bonded polyolefin material easily and without tearing.

According to the present invention therefore a process for producing a package for a product includes placing the product on a wall of spun bonded polyolefine material, draping a thermo-formable film over the product before or after softening by heat, and creating a fluid pressure differential between the film and the spun bonded polyolefin material to cause the film to be drawn or pressed over the product to cause it to heat seal itself to the wall at areas of mutual contact.

In a convenient method the pressure differential is caused by a vacuum which draws the film over the product.

Preferably the wall is provided with a base made from a porous material which is heat bonded thereto and the material may, for example, be paperboard or cardboard.

The wall itself is preferably made from material manufactured by Dupont & Company and sold under the Registered Trade Mark TYVEK.

In order to allow visibility of the product the thermoformable film may be transparent and may, for example, by polyethelene.

Due to the characteristics of the spun bonded polyolefin material the wall provided by it is bacteria resistant and where the two layers of material are sealed together they can be readily peeled apart when the package is to be opened. The wall may be provided with a base made from a porous material and this may be heat bonded to it, and the material may for example be paperboard or cardboard.

If desired the base may be heat bonded and the film heat sealed to the wall simultaneously.

In order to facilitate the heat sealing the wall may have a heat seal coated side.

Preferably radiant heat is used to heat seal the base to the wall and/or the wall to the film, and to soften the film.

The process preferably uses spun bonded polyolefin material manufactured by Dupont & Company and sold under the Registered Trade Mark TYVEK. In order to allow visibility of the product the thermoformable film may be transparent and may conveniently be polyethylene. If desired part of the edge of the material may not be bonded to the wall to facilitate opening.

In any case, the package may also include an outer blister covering made from a plastics material such as a cellulose acetate and if desired this may be housed in a rigid container such as a cardboard box.

Also included in the invention is a package made according to the process set forth above.

The invention can be performed in many ways but one process and a package according to the invention will now be described by way of example and with reference to the accompanying drawings in which:

FIG. 1 is a cross-sectional end elevation of a package for a surgical implant,

FIG. 2 is a side view of the package shown in FIG. 1 with various parts ready for assembly, FIG. 3 is a cross-sectional side view of the finished complete package ready for despatch, and FIG. 4 is a plan view of the package shown in FIG. 3.

The package to be described is for a hip prosthesis which is indicated in the drawings by reference numeral 1. The process for packaging the prosthesis 1 according to the invention is carried out as follows:

A sheet of spun bonded polyolefin material 2 of the kind manufactured by Dupont & Company and sold under the Registered Trade Mark TYVEK is placed over a sheet of paperboard 3. The lower surface of the spun bonded material 2 is heat seal coated to assist the bonding of this material to the paperboard at a later stage of the process.

The prosthesis 1 is now placed on the laminate produced by the sheets 2 and 3 and a thermo-formable film 4 of clear polyethelene is draped over the prosthesis. Radiant heat is now applied which causes the film 4 to soften and a vacuum is applied through the paperboard sheet 3 and spun bonded polyolefin sheet 2 which causes the softened film 4 to be drawn over the prosthesis 1 and to follow its contours. The edges of the film 4 heat seal themselves to the surface of the polyolefin sheet 2 where they are in mutual contact as indicated in FIG. 1. The edges of the package can now be trimmed as required.

The result is a package which can be sterilized and hold sterility as the polyolefin sheet 2 is bacteria resistent as is the film 4.

In order to assist opening of the package a strip of printed cellulose acetate tape or similar material with the legend "peel here" can be attached to the sheet 2 adjacent one edge so that when the edge sealing takes place this prevents the formation of a heat seal at this point and thus enables the two sheets to be easily separated and the film 4 pulled away from the sheet 2 when it is necessary to open the package thus obviating any debris such as is normally caused when a heat sealed film of this kind is torn away from a paperboard backing to which it has been directly sealed. This thus assists in maintaining sterile conditions.

The vacuum is usually applied through a forming table of known kind.

It will be appreciated that in an alternative process, not shown, the paperboard sheet 3 could be omitted but it is usually advantageous to include it as it provides a stiffening effect.

Again, if desired the polyolefin sheet 2 could be heat sealed to the paperboard sheet 3 prior to placing the prosthesis 1 in position and covering the latter with the film, cover, or skin 4.

As shown in FIGS. 1 and 2 therefore it will be seen that the package comprises the cover 4 of thermo formable film which extends around part of the prosthesis 1, which is the product, and this film 4 is sealed to a wall which is provided by the spun bonded polyolefin material sheet 2. The paperboard sheet 3 acts as a base. Due to the fact that the thermo-formable film 4 is made from clear polythene the product can be easily viewed.

In order to provide further protection for the product an outer covering is provided by a conventional "blister pack" made from cellulose acetate material and indicated in FIGS. 3 and 4 by reference numeral 5. The heat sealing method therefore provides the prosthesis with an inner barrier of what is now in effect a double pack the outer consisting of the blister pack 5. It will be appreciated that in certain circumstances the outer covering may not be necessary.

In order to further protect the product during storage or despatch the outer blister pack 5, which is also made from a clear material, is placed in a rigid container in the form of a cardboard box 6 and a lid 8. The lower portion 7 is provided with a layer of foam material 9 to provide further protection and enhance the appearance of the pack and suitable graphics can be provided on the lid.

Due to the fact that the blister pack 5 is made from a clear plastics material the prosthesis 1 can be easily viewed when the lid 8 of box is removed but if necessary a lead 10 of the prosthesis 1 can be wrapped in a cotton sock or covered by a felt bag to provide further protection.

It has been found that the material sold by Dupont Limited under the Trade Mark SURLYN is also suitable for use as the thermoformable film 4.

In an alternative method the vacuum could be replaced by applying air or gas pressure from above the film to cause it to be pressed over the prosthesis 1 and the edges of the film to heat seal themselves to the surface of the sheet 2.

What is claimed is:

1. A process of producing a package for a product comprising the steps of providing a first wall of porous spun bonded polyolefin material of a first predetermined thickness as defined between first and second opposite faces thereof, providing a second wall of porous material of a second predetermined thickness as defined between first and second opposite faces thereof, said second predetermined thickness being greater than said first predetermined thickness, disposing a coating between said first faces for adhering the first and second porous walls together, placing a product on the second face of the first wall, draping a thermoformable film over the product and a portion of the first wall second face outboard of the product, heating the film, drawing the film against the product and the first wall second face portion by a vacuum drawn through the porous walls and the coating therebetween, thereby bonding the drawn film to the first wall second face during the drawing operation.

2. The process as defined in claim 1 including the step of adhering the first and second porous walls together by the coating therebetween during the performance of the drawing/heating steps.

3. The process as defined in claim 2 wherein the coating is a heat bondable material.

4. The process as defined in claim 3 including the step of packaging the package thus formed in an outer blister covering.

5. The process as defined in claim 4 including the step of housing the blister covering in a rigid outer container.

6. The process as defined in claim 5 wherein the coating step is performed by applying a heat seal coating to the first face of the first wall prior to the performance of the drawing step.

7. The process as defined in claim 6 wherein the coating step is performed utilizing a heat seal coating, and the first and second walls are adhered to each other by the heat seal coating during the performance of the heating and vacuum drawing steps.

* * * * *